US005396891A

United States Patent [19]

Whitney et al.

[11] Patent Number: 5,396,891
[45] Date of Patent: Mar. 14, 1995

[54] SYSTEM AND METHOD FOR EXTERNAL ACOUSTIC BONE VELOCITY MEASUREMENT

[75] Inventors: Hartwell H. Whitney; Roy E. Laudenslager, both of Portland, Oreg.

[73] Assignee: Osteo Sciences Corporation, Beaverton, Oreg.

[21] Appl. No.: 43,870

[22] Filed: Apr. 7, 1993

[51] Int. Cl.6 .............................................. A61B 8/00
[52] U.S. Cl. ............................................... 128/661.03
[58] Field of Search ................... 128/660.01, 660.02, 128/660.06, 661.03, 662.03

[56] References Cited

U.S. PATENT DOCUMENTS

| Re. 32,782 | 11/1988 | Pratt, Jr. | 128/660 |
|---|---|---|---|
| 2,763,153 | 9/1956 | Simjian | 128/661.03 |
| 3,695,252 | 10/1972 | Gordon | 128/2 V |
| 3,847,141 | 11/1974 | Hoop | 128/2 V |
| 4,059,010 | 11/1977 | Sachs | 73/596 |
| 4,074,564 | 2/1987 | Anderson | 73/596 |
| 4,322,974 | 4/1982 | Abele et al. | 73/602 |
| 4,361,154 | 11/1982 | Pratt, Jr. | 128/660 |
| 4,421,119 | 12/1983 | Pratt, Jr. | 128/660 |
| 4,437,468 | 3/1984 | Sorenson et al. | 128/662.03 |
| 4,437,473 | 3/1984 | Mollan | 128/773 |
| 4,453,550 | 6/1984 | Flax | 128/660 |
| 4,621,645 | 11/1986 | Flax | 128/660 |
| 4,649,933 | 3/1987 | Jackson | 128/774 |
| 4,669,482 | 6/1987 | Ophir | 128/660 |
| 4,677,981 | 7/1987 | Coursant | 128/660 |
| 4,679,565 | 7/1987 | Sasaki | 128/660 |
| 4,680,966 | 7/1987 | Nicolas | 73/597 |
| 4,682,608 | 7/1987 | De Rigal et al. | 128/774 |
| 4,683,893 | 8/1987 | Mayo | 128/660 |
| 4,688,581 | 8/1987 | Moss | 128/741 |
| 4,754,763 | 7/1988 | Doemland | 128/739 |
| 4,774,679 | 9/1988 | Carlin | 364/550 |

(List continued on next page.)

OTHER PUBLICATIONS

WO90/0190 (Published Intnl Appln #PCT/US89/03412) published 8 Mar. 1990 to Brandenburger et al.

Ashman, Richard B. et al., "Elastic Properties of Cancellous Bone: Measurement by an Ultrasonic Technique", 20 (No. 10) J. Biomechanics (1987), pp. 979–986.

Ashman, Richard B. et al., "A Continuous Wave Techniques for the Measurement of the Elastic Properties of Cortical Bone" 17 (No. 5) J. Biomechanics (1987), pp. 349–381.

Baran, Daniel T., et al., "Ultrasound Attenuation of the Os Calcis in Women with Osteoporosis and Hip Fractures", 43 Calcified Tissue International (1988), pp. 138–142.

Evans, G. Paul, et., Proceedings of Ultrasonic Assessment of Bone II, Symposium organized by Harwell Biomedical Research, (Jun. 23, 1992, Bath England).

Faulkner, Kenenth G. et al., "Noninvasive Measurements of Bone Mass, Structure, and Strength: Current Methods and Experimental Techniques", 157 AJR (1991), pp. 1229–1237.

Johnston, Jr., C. Conrad et al., "Current Concepts—Clinical Use of Bone Densitometry", 324 (No. 16), New England Journal of Medicine (1991), pp. 1105–1109.

Kwon S. J., et al., "Sonic Diagnosis of Bone Fracture (List continued on next page.)

Primary Examiner—Francis Jaworski
Attorney, Agent, or Firm—Bromberg & Sunstein

[57] ABSTRACT

An ultrasonic system for determination of bone characteristics is provided having first and second transducers in a mounting arrangement for mounting the transducers in spaced relationship with respect to the bone, the mounting arrangement including a contact arrangement for defining a stable and repeatable contact point on the body part containing the bone, such that the transducers may be biased against the body part with a substantially constant force, the contact arrangement including a plurality of contact buttons projecting in a common direction, the buttons being axially displaceable and fitted with an engagement sensing arrangement for determining contact with the body part such that operation of the device may be inhibited until proper contact is made.

11 Claims, 10 Drawing Sheets

U.S. PATENT DOCUMENTS

| | | | |
|---|---|---|---|
| 4,774,959 | 10/1988 | Palmer et al. | 128/660 |
| 4,799,498 | 1/1989 | Collier | 128/774 |
| 4,836,218 | 6/1989 | Gay et al. | 128/773 |
| 4,855,911 | 8/1989 | Lele et al. | 364/413 |
| 4,913,157 | 4/1990 | Pratt, Jr. et al. | 128/661 |
| 4,926,870 | 5/1990 | Brandenburger | 128/660 |
| 4,930,511 | 6/1990 | Rossman et al. | 128/661 |
| 4,941,474 | 7/1990 | Pratt, Jr. | 128/660 |
| 4,949,312 | 8/1990 | Iwasawa | 367/7 |
| 4,949,313 | 8/1990 | Iwasawa | 367/7 |
| 4,976,267 | 12/1990 | Jeffcott et al. | 128/660 |
| 5,006,984 | 4/1991 | Steele | 364/413 |
| 5,014,970 | 5/1991 | Osipov | 269/328 |
| 5,038,787 | 8/1991 | Antich et al. | 128/660 |
| 5,042,489 | 8/1991 | Wiener et al. | 128/661 |
| 5,052,394 | 10/1991 | Carpenter et al. | 128/660 |
| 5,054,490 | 10/1991 | Rossman et al. | 128/661 |
| 5,079,951 | 1/1992 | Raymond et al. | 73/602 |
| 5,095,909 | 3/1992 | Nakayama et al. | 128/660 |
| 5,099,849 | 3/1992 | Rossman et al. | 128/661 |
| 5,119,820 | 6/1992 | Rossman et al. | 128/661 |
| 5,134,999 | 8/1992 | Osipov | 128/661.03 |
| 5,143,069 | 9/1992 | Kwon et al. | 128/660 |
| 5,197,475 | 3/1993 | Antich | 128/660.01 |
| 5,218,963 | 6/1993 | Mazess | 128/661.03 |
| 5,259,384 | 11/1993 | Kaufman et al. | 128/660 |

OTHER PUBLICATIONS and Diseases: Time Series and Frequency Analysis", Ultrasonic Symposium (1986), pp. 949–952.

Lowet, G., et al., "Monitoring of bone consolidation by ultrasound velocity measurement" pp. 2129–2130.

McCloskey, E. V., et al., "Broadband ultrasound attenuation in the os calcis: relationship to bone mineral at other skeletal sites", 78 Clinical Science (1990), pp. 227–233.

McCloskey, E. V., et al., "Assessment of broadband ultrasound attenuation in the os calcis in vitro", 78 clinical Science (1990), pp. 221–225.

McKelvie, M. L., et al., "In vitro Comparison of Quantitative Computed Tomography and Broadband Ultrasonic Attenuation of Trabecular Bone", 10 Bone (1989), pp. 101–104.

Porter, P. W., et al., "Prediction of hip fracture in elderly women: a prospective study", 301 Br. Med. J. (1990), pp. 638–641.

Saha, S., et al., "The effect of soft tissue on wave—propagation and vibration tests for Determining the in vivo properties of bone", (vol. 10) Pergamon Press (1977), pp. 393–401.

Sonstegard, David, A., et al., "Sonic Diagnosis of Bone Fracture Healing—A Preliminary Study" pp. 689–694.

Tavakoli, M. B., and J. A. Evans, "Dependence of the velocity and attenuation of ultrasound in bone on the mineral content", 36 (No. 11) Phys. Med. Biol. (1991), pp. 1529–1537.

Wright, T. M., et al., "Soft Tissue Attenuation of Acoustic Emission Pulses", (vol. No. 105). Journal of the Biomechanical Engineeing (Feb. 1983), pp. 20–23.

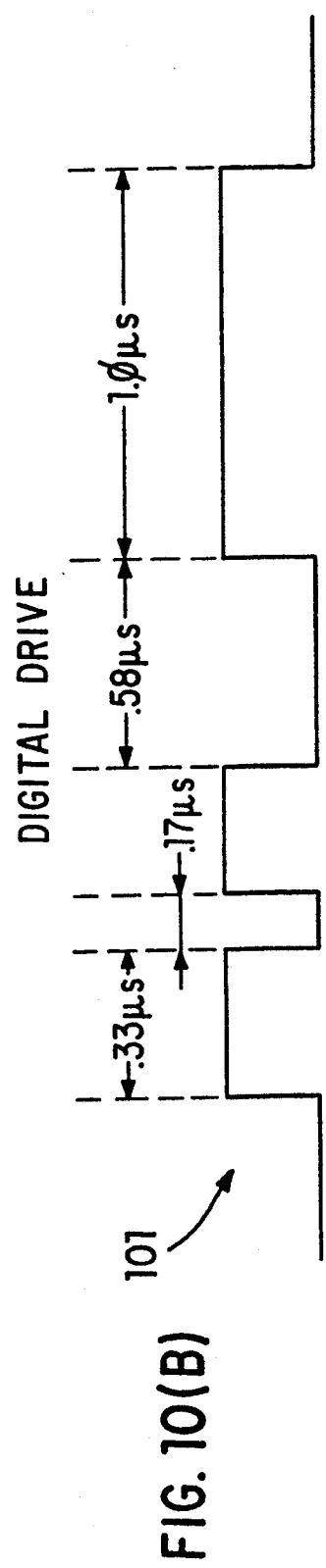
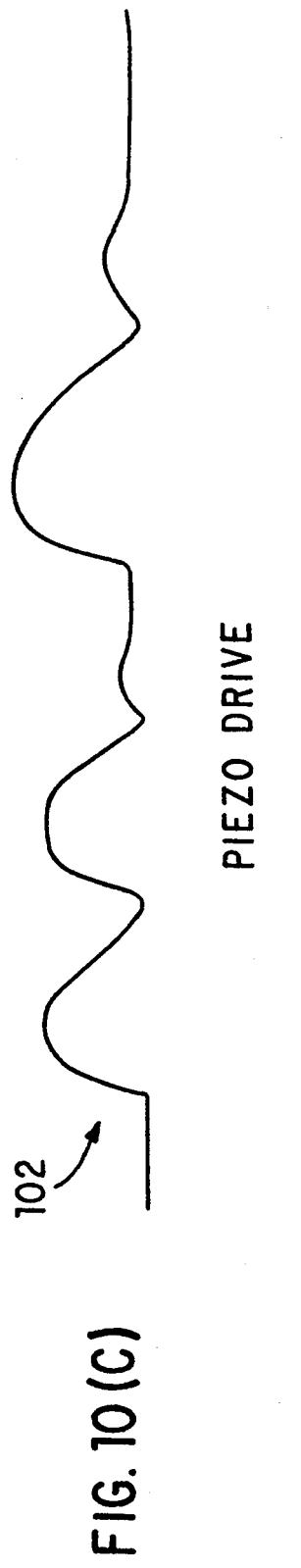
FIG. 10(B)
FIG. 10(C)
FIG. 10(A) CODE REPRESENTATION: 1111011101111100000001111111111111

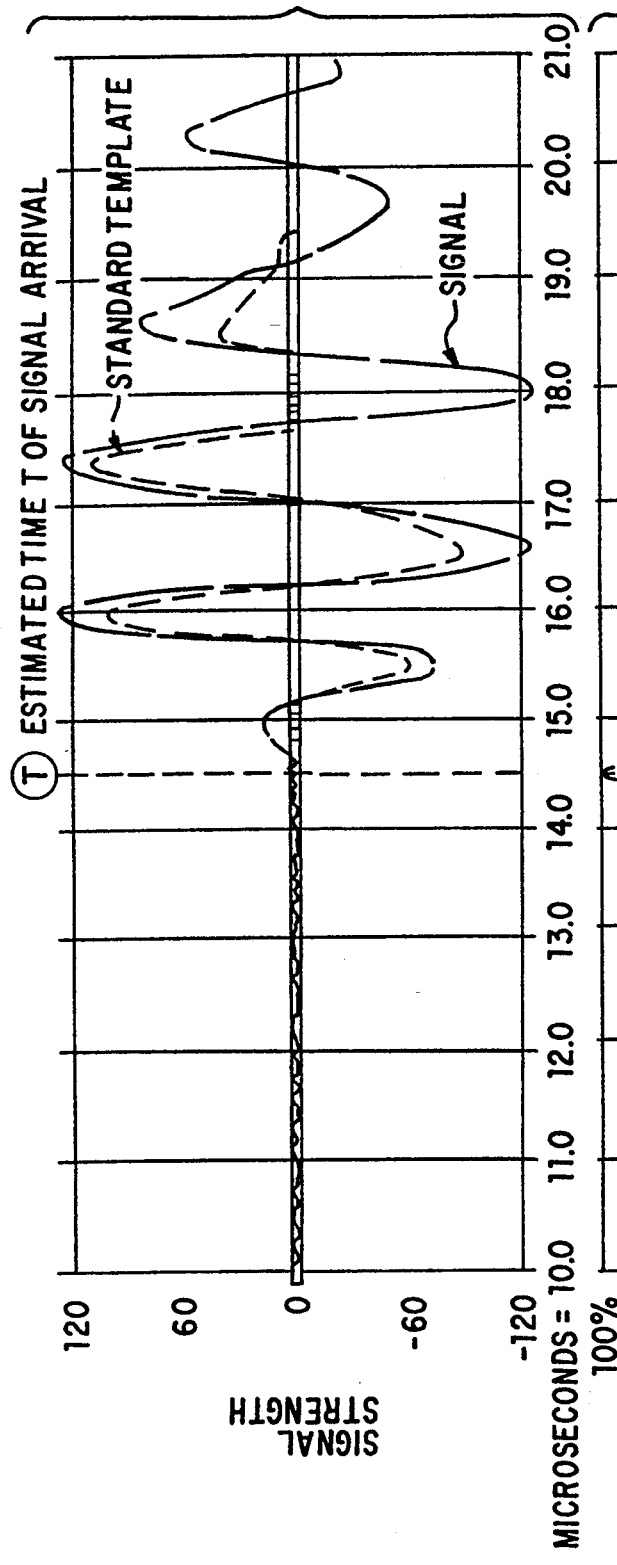
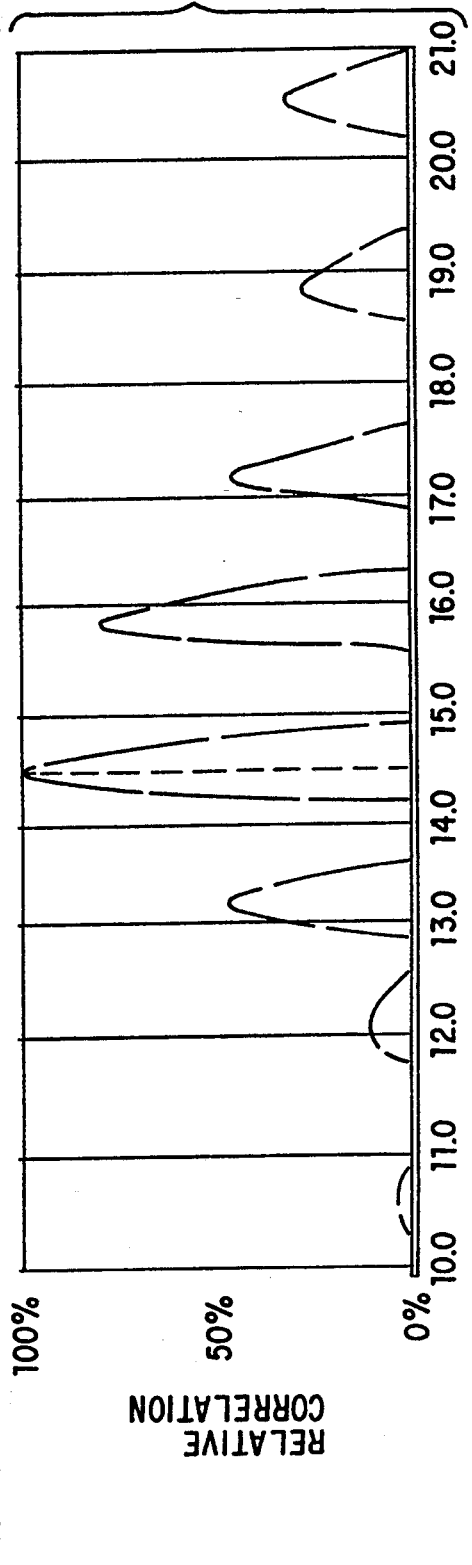

SYSTEM AND METHOD FOR EXTERNAL ACOUSTIC BONE VELOCITY MEASUREMENT

TECHNICAL FIELD

The present invention relates to systems and methods for measuring the velocity of acoustic waves in bones of vertebrates, and more particularly to systems and methods for accomplishing the measurement externally of the subject.

BACKGROUND ART

It is known to perform bone velocity measurement of a subject externally of the subject. Systems typically assume that bones of interest have isotropic propagation characteristics in a plane perpendicular to the longitudinal axis of the bone. U.S. Pat. No. 4,421,119, issued for an invention of Pratti Jr., teaches the use of a pair of opposed transducers for bone velocity measurement. A first transducer is used as a transmitter, and a second transducer is used as a receiver. The transit time of a sound pulse from the transmitter to the receiver can be used to determine bone velocity. It is known to use both continuous waves and pulsed waves to drive the transmitting transducer. Ashman, et al., "A Continuous Wave Technique for the Measurement of the Elastic Properties of Cortical Bone," 17 J. Biomechanics 349-361, 353 (No. 5) (1964). The continuous wave method has been viewed as more accurate, because with pulse propagation, a certain amount of error is introduced in reading the start of the received signal. With the continuous wave approach, however, the phase shift between the two signals can be used to determine the time delay of propagation. Id. However, determining the phase shift can involve ambiguity in the number of periods of delay, which can be resolved by determination of the phase shift separately and a number of different frequencies, graphically plotting the delay, and finding the appropriate intercept of the plot. Id., at 360-361.

In operation of either pulses or the continuous wave approach, furthermore, there is inherent difficulty in dealing with multipath. That is, there is typically more than one path for a waveform to reach the receiving transducer. Finding the transmitted waveform over the path of choice at the receiver poses difficulties for the designer.

SUMMARY OF THE INVENTION

The present invention overcomes problems in the prior art in finding the transmitted waveform over the path of choice at the receiver, and provides in various embodiments a convenient system and method for bone velocity measurement.

In one embodiment, the invention provides a system for externally measuring in a vertebrate subject the velocity of an acoustic wave in a bone that has a longitudinal axis. The system in this embodiment as first and second transducers, each of which has a central acoustic axis. A mounting arrangement mounts the transducers so that their central axes form an angle substantially less than 180 degrees and lie substantially in a plane that is disposed transversely with respect to the longitudinal axis of the bone. A signal exciter provides an electrical signal to the first transducer to cause it to produce an acoustic wave that is propagated into the subject and received by the second transducer along a path that includes a chord of the bone. A signal processing arrangement in communication with the second transducer and the signal exciter determines the velocity of the acoustic wave in the bone. The angle of the axes of the transducers may be optimized to reduce the error in apparent bone velocity measurement caused by soft tissue thickness variation, and the plane may be substantially perpendicular to the longitudinal axis of the bone.

In a further embodiment, three transducers are employed, mounted in spaced relationship with respect to the bone. A signal exciter provides an electrical signal to the first transducer to cause it to produce an acoustic wave that is propagated into the subject and received by the second and third transducers along first and second paths respectively through the bone and including soft tissue. A signal processing arrangement in communication with the second and third transducers and the signal exciter determines the velocity of the acoustic wave in the bone. The processing arrangement includes means for effectively determining the difference in the wave transit time between the first and second transducers from that between the first and third transducers in the course of determining the velocity between the second and third transducers, so as to reduce by cancellation the error in bone velocity determination caused by soft tissue. A yet further embodiment includes an arrangement for interchanging the roles of the first and third transducers so that the third transducer is used to produce an acoustic waveform and the first transducer is in communication with the processing means. The processing arrangement further includes (i) an arrangement for effectively determining the difference in the wave transit time between the third and second transducers from that between the third and first transducers in the course of determining the velocity between the second and third transducers and (ii) an arrangement for averaging the velocity determinations made with and without operation of the interchange arrangement.

In another embodiment, the invention provides a system for velocity measurement of an acoustic wave in a bone disposed in a body part. The system has first and second transducers, a mounting arrangement for mounting the transducers in spaced relationship with respect to the bone, a signal exciter, and a velocity determination arrangement. The mounting means in this embodiment includes a contact arrangement for contacting the body part and defining a stable and repeatable position on the body part. The transducers may be mechanically biased to urge them against the body part with substantially constant force. The contact arrangement may be implemented with a plurality of contact buttons (usefully four in many embodiments) projecting in a common direction for contacting the body part. In a further embodiment, the contact buttons may be axially displaceable and fitted with an engagement sensing arrangement for determining when each button has been placed firmly in contact with the body part. Operation of the system may be inhibited unless and until the engagement sensing arrangement has determined that each button has been placed firmly in contact with the body part. A temperature sensor may be disposed in one of the contact buttons to sense the temperature of the body part.

In still another embodiment, the invention provides a system for externally measuring the velocity of an acoustic wave in a bone of a subject, and the system has first and second transducers, and an arrangement for mounting the transducers in spaced relationship with respect to the bone. A signal exciter provides a signature waveform to the first transducer to cause it to produce a characteristic acoustic waveform that is propagated into the subject and received by the second transducer along a path that includes the bone. A template arrangement provides a standard template waveform that is indicative of a signature waveform received by the second transducer.

An association arrangement associates the standard template waveform with the waveform received by the second transducer, so as to discriminate against wave patterns other than the signature waveform and to ascertain the transit time of the signature waveform along the path. The signature waveform may be an irregular continuous wave optimized to provide enhanced discrimination by the association arrangement, and may be fewer than ten (for example, three) cycles long. The standard template waveform may be derived by empirical selection from representative sample signals present at the second transducer. The association means may be a correlator for cross correlating the standard template waveform with the waveform received by the second transducer. The correlator may operate on sampled signals representing the standard template waveform and the waveform received by the second transducer; in such a case there may be included an arrangement for refining the determination of the transit time of the signature waveform by interpolation.

BRIEF DESCRIPTION OF THE DRAWINGS

The foregoing features of the present invention will be more readily understood by reference to the following detailed description taken with the accompanying drawings, in which:

FIGS. 10(a) through 10(c) show the digital pattern, resulting pulse waveform and exciter waveform at the terminals of transducer 11, respectively, for the embodiment of FIG. 4;

FIG. 11 is a graph showing, in the top half, the standard template waveform and the waveform received at the second transducer and, in the bottom half, the cross correlation of these two waveforms;

DETAILED DESCRIPTION OF SPECIFIC EMBODIMENTS

Figure 1:
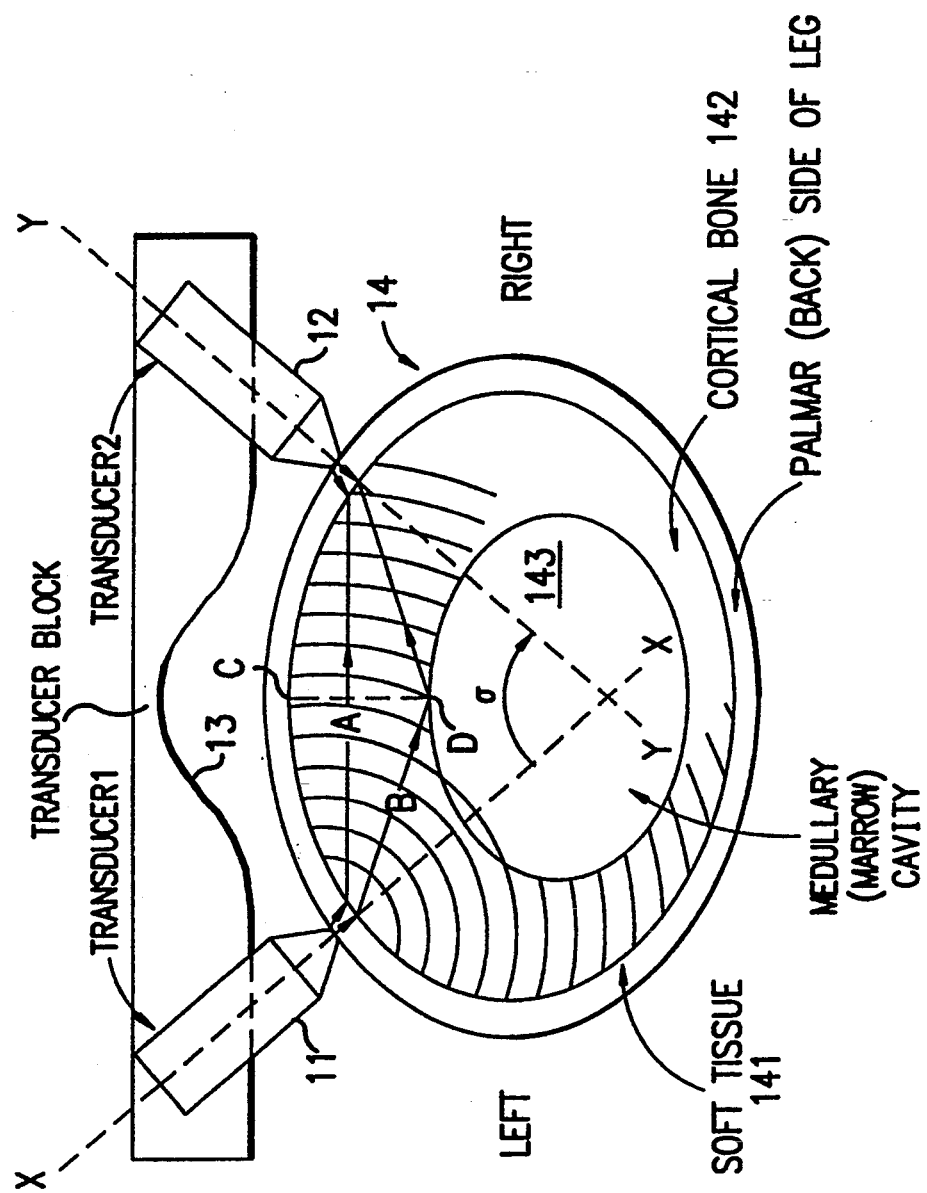
FIG. 1 is a diagram of a preferred embodiment of the invention showing transducers configured to measure sound velocity through a chord of a bone of an vertebrate subject.

In FIG. 1 is presented a diagram of a preferred embodiment of the invention. In this embodiment, first and second ultrasound transducers 11 for transmitting and 12 for receiving respectively an acoustic waveform have central acoustic axes X—X and Y—Y respectively. The transducers are mounted in substantially fixed relation to one another in a transducer block 13, so that their central axes X—X and Y—Y lie in a plane and form an angle $\theta$ that is substantially less than 180 degrees. Various angles are suitable, and may include, for example, zero, 30, 60, 90, 120, and 150 degrees. A body part 14 of a vertebrate subject (such as the leg of a horse or the forearm of a human, for example) includes soft tissue 141 and a bone 142. The bone may be any of a wide variety of bones, including, but not limited to, radius, ulna, third metacarpal, patella, clavicle, and os calcis (calcaneus). The bone 142 is here a cortical bone with medullary canal 143, and the bone 142 has a longitudinal axis (not shown) that is perpendicular to the page. The transducer block 13 is oriented so that the plane defined by central axes X—X and Y—Y is transverse (and here perpendicular) to the longitudinal axis of the bone 142. In a series of experiments, we have found, surprisingly, that this embodiment, employing non-opposed transducers, provides a path A between the transducers 11 and 12 that includes a chord of the bone 142.

Since the distance between transducers 11 and 12 is fixed by the transducer block 13 and is determinable, the length of path A can be reasonably estimated; a measurement of the transit time of an acoustic wave over path A can therefore be used to determine the velocity of an acoustic wave in the bone 142 over this path. Accordingly, a signal processing arrangement is employed to measure the transit time and to determine the velocity.

Although path A has the shorter transit time for an acoustic waveform traveling between the two transducers, there is another path B running from the first transducer 11 to the boundary of the medullary canal 143 and from there to the second transducer 12. With the bone velocity determined in the manner described above with respect to measurement of waveform transit time over path A, it is possible to use a waveform transit time measured over path B to estimate the thickness c-d of the bone. It is possible to measure the waveform transit time over path B with a judiciously selected waveform, because the waveform over this path will arrive at transducer 12 after the waveform over path A, and is therefore detectable.

Figure 2:
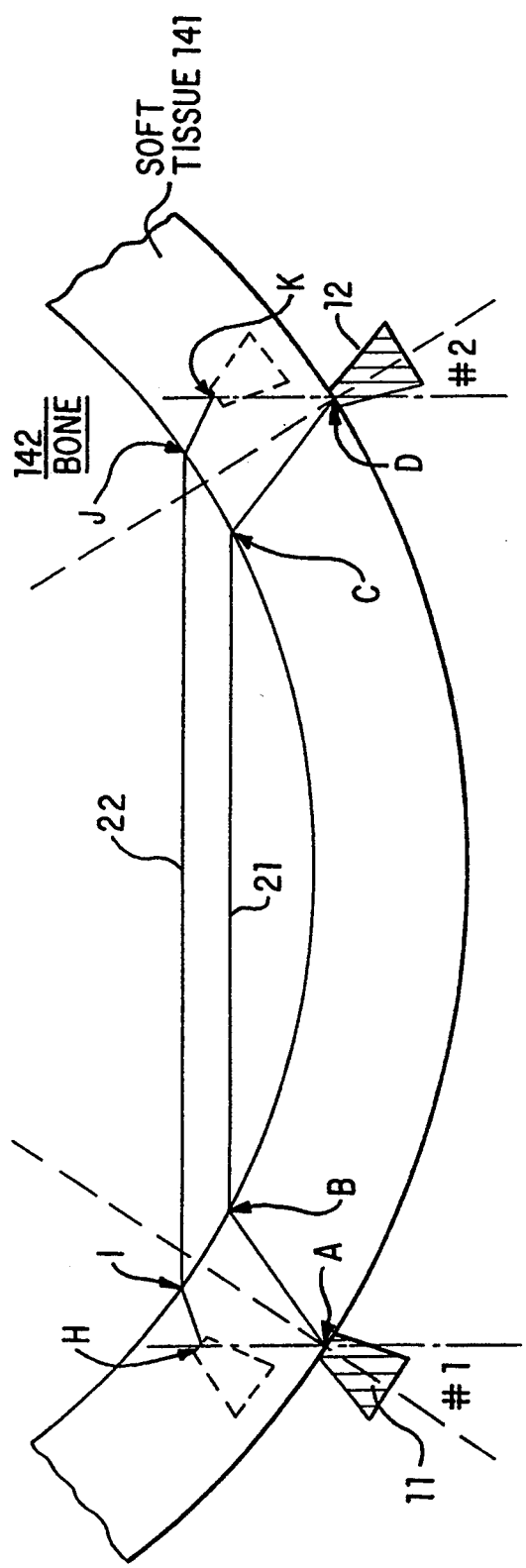
FIG. 2 is a diagram illustrating the relative insensitivity of the embodiment of FIG. 1 to compression of the transducers into soft tissue of the subject.

A potential difficulty with the embodiment shown in FIG. 1, as with all other embodiments employing acoustic velocity measurement techniques external to the subject, is the transit time of the waveform through soft tissue 141. The soft tissue transit time introduces potential inaccuracies in bone velocity measurement. A number of strategies may be employed in accordance with the present invention to deal with this effect. In accordance with a preferred embodiment, the angle $\theta$ may be optimized to reduce the effect of soft tissue transit time. As shown in FIG. 2, there is a regular path 21 including soft tissue segments AB and CD through a first chord BC of bone 142 between the transducers 11 and 12. If, due to compression of the soft tissue 141 or the use of the system on another subject simply having less soft tissue 141, there will be a different path 22, including soft tissue segments HI and JK through a second chord IJ of bone 142. A knowledge of Snell's law, the pertinent indices of refraction, and velocities of ultrasound in the soft tissue 141 and the bone 142, the approximate dimensions of the body part 14 and of the bone 142 and soft tissue 141, permits determination of an angle $\theta$ in FIG. 1 with which the path lengths 22 and 21 are such that transit time of a waveform over path 22 is approximately equal to the transit time of a waveform over path 21. Such a determination can be made by one of ordinary skill in the art; a first order determination of $\theta$ can be made by assuming the velocity through the two media is constant. Snell's law gives the angles of refraction at the boundary of bone and soft tissue. The angle $\theta$ can then be determined using simple trigonometry. A further iteration on the determination can compensate for the slower velocity through soft tissue. Note that in path 22 the greater length of the chord IJ (in comparison to the length of chord BC in path 21) compensates for the shorter lengths of soft tissue segments HI and JK (in comparison to the lengths of segments AB and CD in path 21). Because, however, the transit time through soft tissue is slower than through bone, the bone chord IJ must be lengthened by an amount greater than the amount by which the cumulative length of segments HI and JK is shortened.

Figure 3:
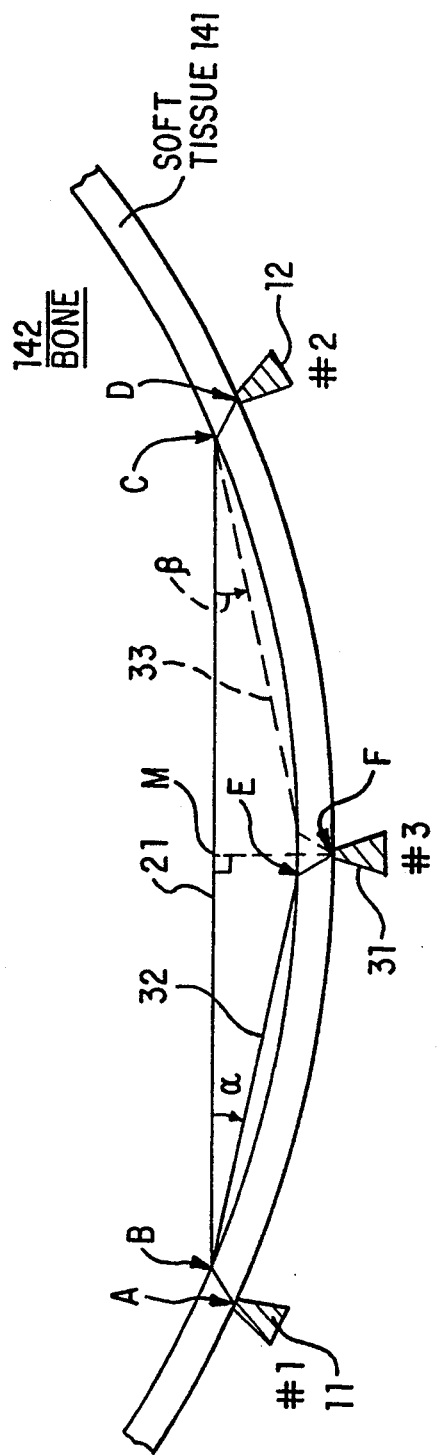
FIG. 3 is a diagram illustrating an embodiment of the invention employing three transducers.

In FIG. 3 is illustrated a further embodiment for compensating for the effect of soft tissue. In this embodiment, in addition to transducers 11 and 12 of FIGS. 1 and 2, there is employed a third transducer 31, which also receives a waveform from transducer 11. In addition to the path ABCD between transducers 11 and 12, there is the path ABEF between transducers 11 and 31. The segment FM is a perpendicular to the chord BC. From this figure, it is clear that when $\alpha$ and $\beta$ are small angles, the lengths BM and BE are approximately equal. If soft tissue paths EF and CD are approximately equal, then the transit time over path MC is equal to the total transit time over the path 21 less the transit time over path 32, since both paths include approximately the same total segment lengths in soft tissue 141. Accordingly, in this embodiment, a signal processing arrangement is employed to determine the difference in the wave transit time between the first and second transducers from that between the first and third transducers. This difference, which is equal to the transit time over path MC, is computed in the course of determining the velocity of ultrasound in bone between the second and third transducers, in a manner as to reduce the error in the determination caused by soft tissue by cancellation. (These determinations are possible when the position of transducer 31 is known relative to the positions of transducers 11 and 12.)

In a further embodiment, the roles of the outside transducers, here 11 and 12, may be interchanged. Transducer 12 is used for transmitting and transducer 11 is used for receiving an acoustic waveform. Thus a first path 21 exists over segments DCBA from transducer 12 to transducer 11. A second path 33 (shown by a dashed line) exists from transducer 12 to transducer 31. In a manner analogous to that described in the preceding paragraph, the transit time for a waveform over the path MB can be computed by determining the difference in the wave transit time between the second and third transducers from that between the third and first transducers. This difference is computed in the course of determining the velocity of ultrasound in bone between the second and first transducers, in a manner as to reduce the error in the determination caused by soft tissue.

Because the path lengths AB, EF and CD through soft tissue may not be equal, a further compensation for soft tissue can be implemented in which the velocity determinations described in the preceding two paragraphs (for chord segments MC and MB respectively) are averaged. That is the velocity determinations made both with and without the interchange of transducers (which can be achieved under computer control) are averaged to further compensate for soft tissue.

FIGS. 4-8 illustrate respectively front, side, back, top, and bottom views of an embodiment of the invention including the arrangement of FIG. 1. This embodiment includes in a single housing 41 for all of the components shown in the block diagram of FIG. 9. This embodiment includes a display 42, a keypad 43, power switch 44, and, as explained below, LED indicators 45 (relating to positioning of the housing in relation to the body part), and 46 and 47 (relating to the accuracy of the measurement). In lieu of the keypad other include input means may be employed, such as a joystick.

The embodiment of FIGS. 4-9 includes a microprocessor (CPU 91) and random access memory (RAM) 92 for storage of both prior history of a given subject as well as statistical averages for groups of subjects. (The prior history in this embodiment optionally includes the entire digitally sampled waveform received by transducer 12 in each such successful past velocity determination.) In operation of the device of this embodiment, the keypad is used to enter the identification of the subject as well as pertinent subject data, and for each measurement of the subject the results are stored as well as the date and time of measurement. This data, as well as the statistical averages, can be accessed by the keypad 43 and displayed in the display 42. The subject's velocity measurements over time can be displayed graphically in the display 42.

The power switch 44 includes a mode when held down in which backlighting for the display is provided along with illumination of the keys in the keypad. This mode is useful when the device is operated in dimly lit barns, for example, in measuring bone velocity in a body part 14 of a horse or other animal. The device is powered by a rechargeable battery that is recharged through alternate power port 83. An auxiliary port 82 is provided for an auxiliary sensor, as well as an asynchronous digital serial port 81 (implemented as a modular telephone jack) for uploading and downloading data stored in RAM 92. To facilitate carrying the device, it is equipped with an anchor bar 51 for attachment of a wrist strap.

The rear of the device includes a curved channel 71 adapted to receive the pertinent body part 14 of the vertebrate subject. The channel 71 is bounded by suitably shaped side walls 52 of the housing 41. The transducers 11 and 12 of FIG. 1 are mounted in a block 13 that is spring loaded in the housing 41 to permit the transducers to be seated as close as possible to the bone 142 with a known and repeatable contact force on the body part 14. Proper seating of the transducers is further assured by the use of four contact buttons 61 mounted in pairs on opposite sides of the channel. These contact buttons are axially displaceable and are also spring loaded. When the device has been placed so that the transducers are properly seated on the body part 14, each contact button 61 is urged inward until it closes an associated attitude switch (collectively attitude sensors 911 in FIG. 9). When some but not all of the attitude switches have been closed, the "position" LED 45 is made to blink, and an optional audible warning may be provided. Operation of the device is inhibited unless and until all attitude switches have been closed. When all attitude switches have been closed, the "position" LED 45 is steadily illuminated. After a successful velocity determination has been made, the "good" LED 46 is illuminated. If in the course of making the velocity determination an error condition has been detected, the "repeat" LED 47 is illuminated. In such a case, the user is required to remove the device from the body part; removal is detected by the attitude switches 911. The device will then not provide a further velocity measurement unless it is placed on the body part again.

One of the contact buttons 61 is further provided with a temperature sensor to monitor the temperature of the body part. Additional temperature sensors are employed to determine ambient air temperature and the temperature of the battery compartment. The battery compartment temperature is sensed to monitor when the battery is fully charged and to disconnect it from the charging circuit when it is fully charged.

In some embodiments it will be convenient to provide the transducers 11 and 12, mounting block 13, and the contact buttons 61 with associated attitude switches and temperature sensors in a separate housing (having for example the general appearance of FIG. 7) from the rest of the device, so that the device would have a sensing head and a main body. The head may be attached mechanically to the body by a universal joint, so that a user holding the device by the body could not inadvertently apply torque to the head, possibly risking uneven transducer pressures or poor sealing of the transducers to the body part 14 when measurements are being taken. Such an approach also permits the use of different removable heads to accommodate different sizes of the body part in question or different body parts altogether.

Figure 9:
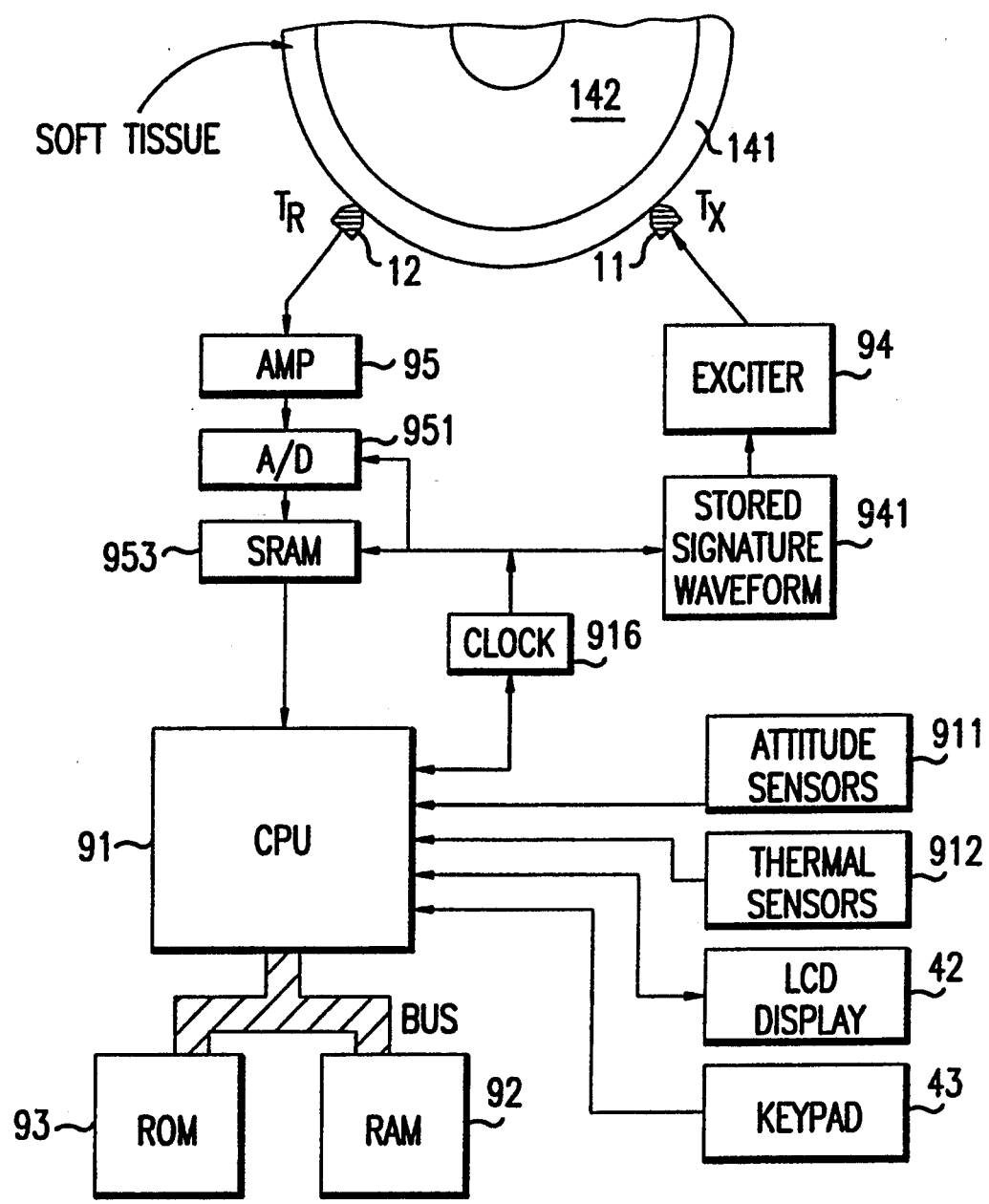
FIG. 9 is a block diagram of the embodiment of FIG. 4.

FIG. 9 shows the structure of the device, which operates under control of CPU 91, in accordance with a program loaded at time of initialization from read only memory (ROM) 93 into RAM 92. A clock 916 times delivery of a stored signature waveform 941 to exciter 94 and transducer 11, which sends the waveform into the body part through soft tissue 141 and bone 142. The waveform is received at transducer 12, is run through amplifier 95, analog-to-digital converter 951, and the sampled digital data is stored in static random access memory (SRAM) 953. A standard template waveform is then cross correlated with the sampled data in SRAM to find the transit time of the signature waveform. The transit time forms the basis of the velocity determination as described above in connection with FIGS. 1 and 2, and the result of the determination is stored in RAM 92 shown in FIG. 9.

FIG. 10 shows the signature waveform employed with the embodiment. The waveform was derived by supplying at the rate of clock 916 (12 MHz) the digital pattern of FIG. 10(A). This pattern is supplied to a pulse waveform generator, the output of which is shown in FIG. 10(B). The pulse generator output is furnished to the primary winding of a step-up transformer, and the secondary of the transformer, providing an output illustrated in FIG. 10(C) is connected to the transducer 11, here implemented by a piezo transducer. In the course of implementing this embodiment of the invention, it has been found that it is dramatically easier to detect and to determine the transit time of the signature waveform by correlation techniques than it is in the case of other waveforms such as ordinary single-repetition rate pulses or single-frequency sinusoidal waves.

FIG. 11 shows the standard template waveform 112 used to correlate with the transducer sampled output 111. The standard template waveform was initially derived from actual transducer outputs obtained with actual body parts, and then empirically modified to produce greater discrimination of the signature waveform. The result of the correlation is shown in the bottom half of FIG. 11. This correlation is performed as discussed in connection with FIG. 12 below.

Figure 4:
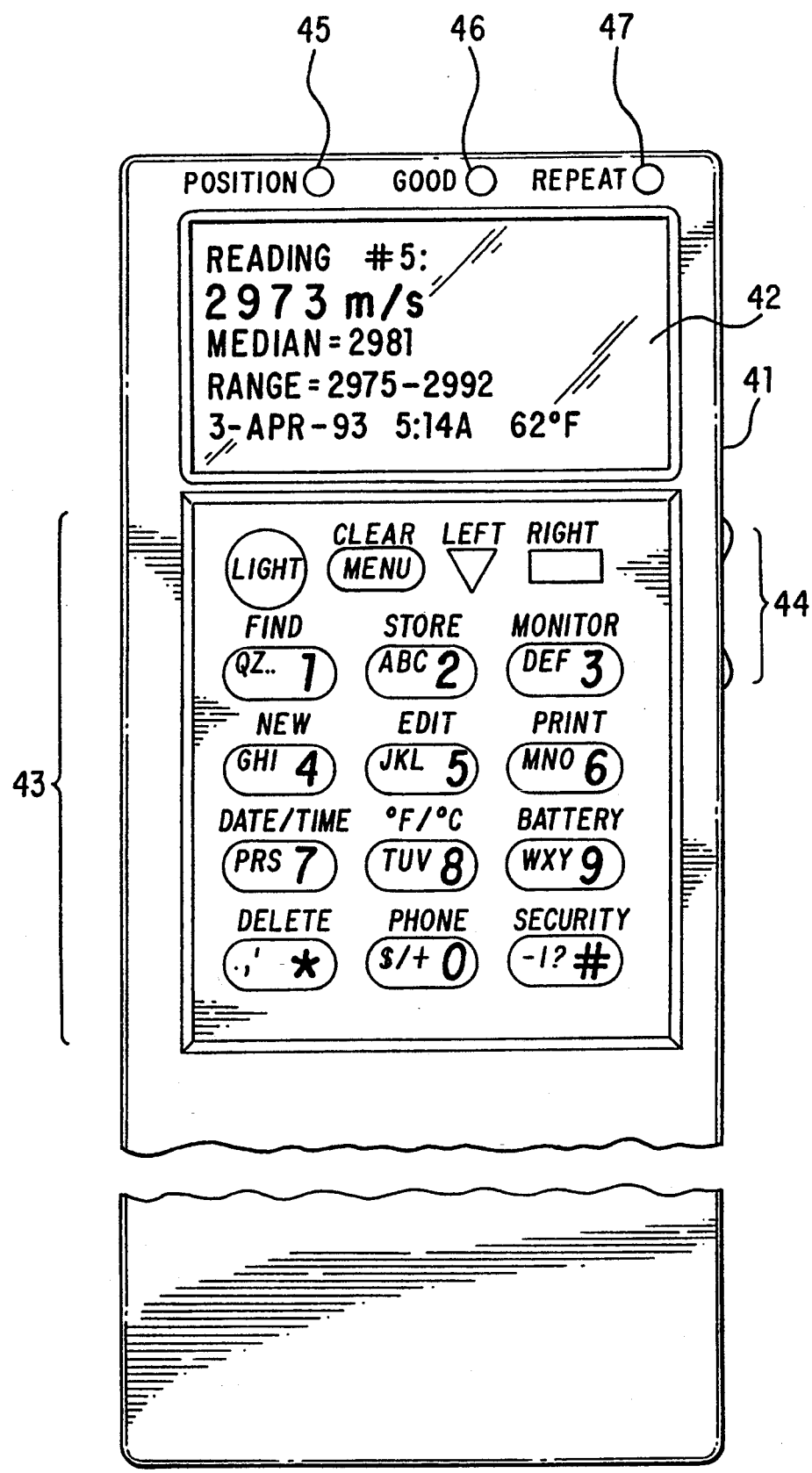
FIG. 4 is a front view of an embodiment of the invention including the arrangement of FIG. 1.
Figure 5:
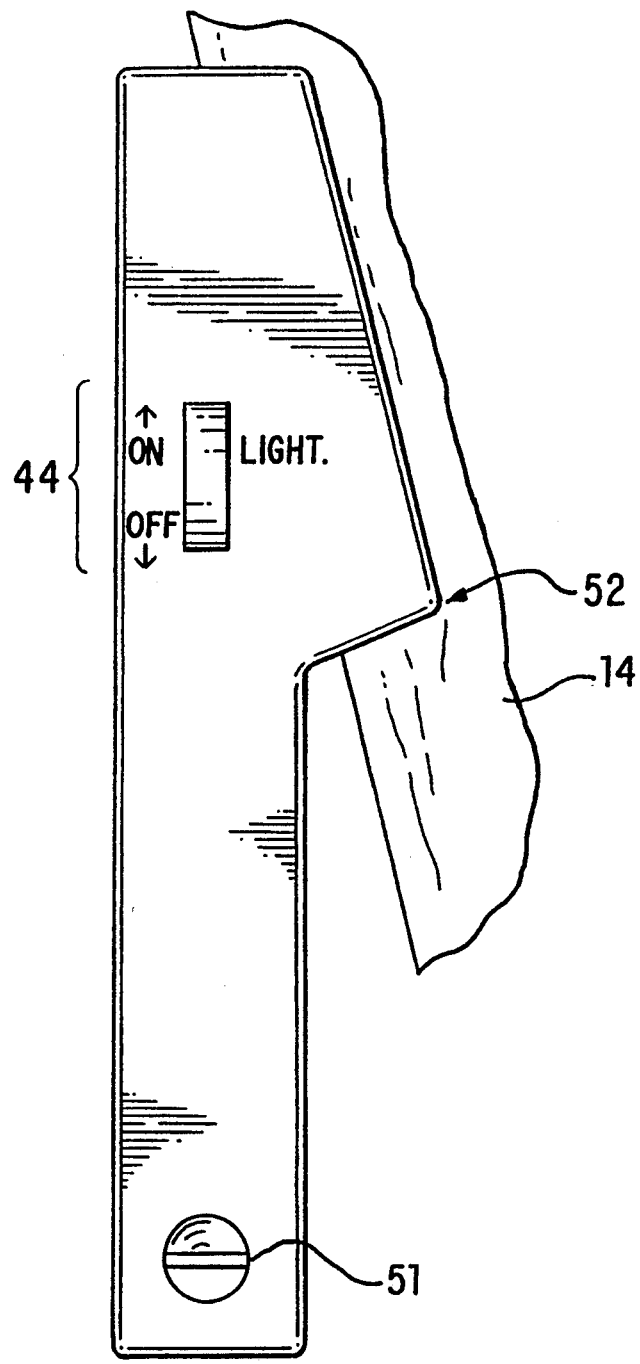
FIG. 5 is a side view of the embodiment of FIG. 4.
Figure 6:
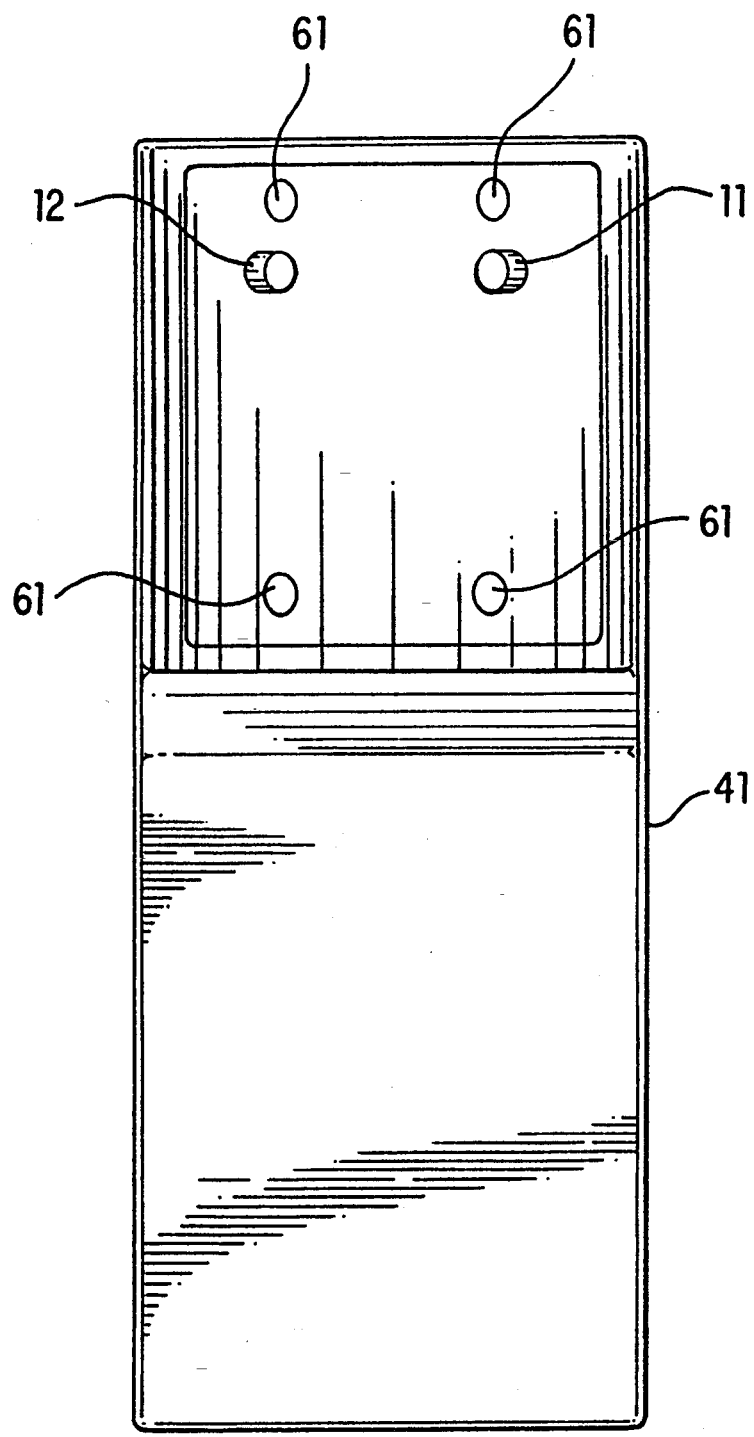
FIG. 6 is a back view of the embodiment of FIG. 4.
Figure 7:
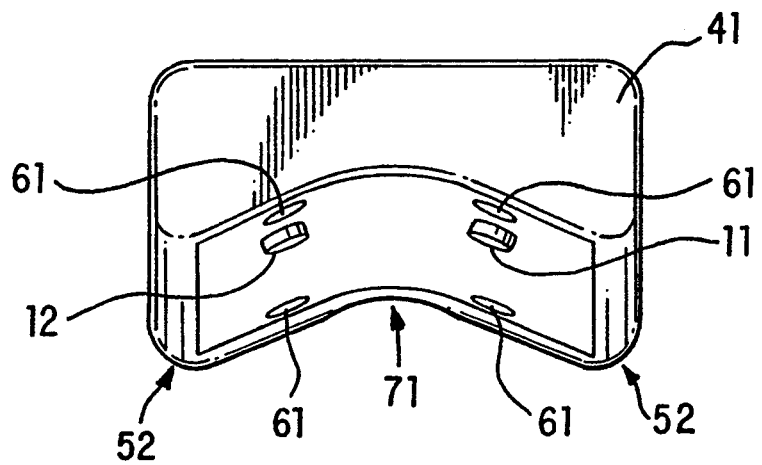
FIG. 7 is a top view of the embodiment of FIG. 4.
Figure 8:
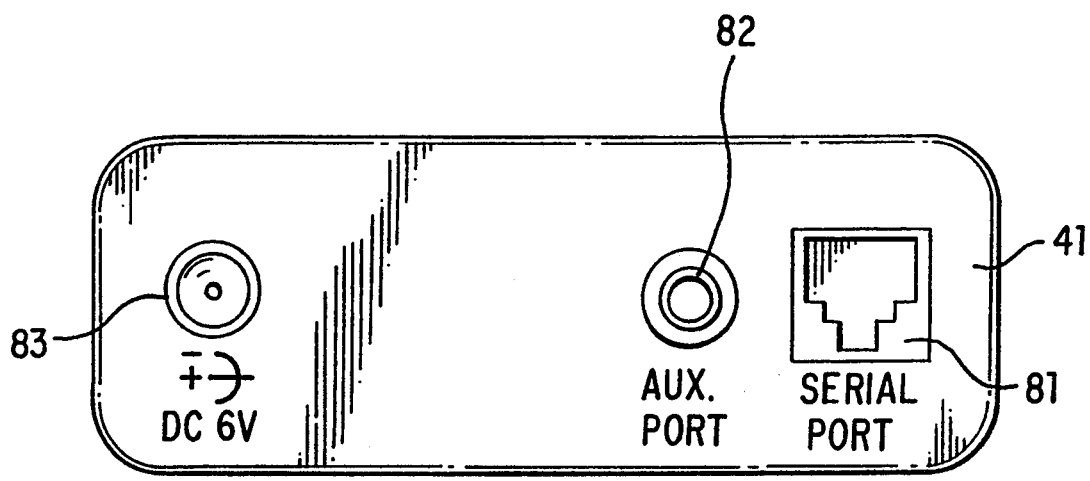
FIG. 8 is a bottom view of the embodiment of FIG. 4.
Figure 12:
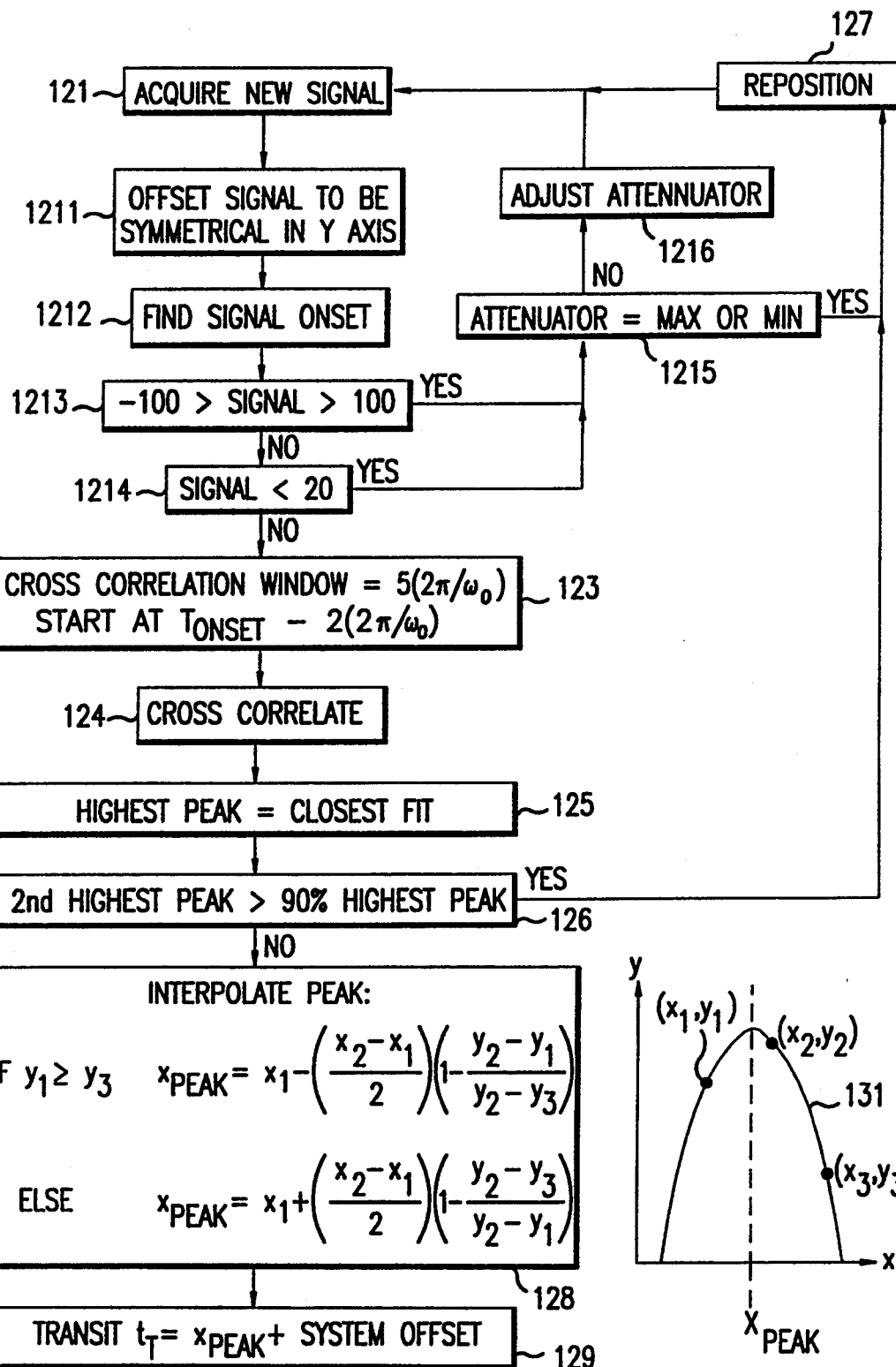
FIG. 12 is a block diagram showing the logical flow in performing the cross correlation and interpolation in the embodiment of FIG. 4.

FIG. 12 is a block diagram showing the logical flow in performing the cross correlation and interpolation in the embodiment of FIG. 4. In step 121, a new digitally sampled signal is loaded into the applicable portion of memory for processing. The signal amplitude (Y-coordinate of each sample) is then offset by an amount sufficient to make it symmetrical about the Y-axis (step 1211). The time (X-coordinate) $t_{onset}$ at which signal onset occurs is then determined (step 1212). The dynamic range of the signal is then tested (steps 1213 and 1214), and if the signal is out of range, the attenuator is adjusted (step 1216) and the signal is reloaded. If (in step 1215) the signal is found to have a dynamic range beyond the adjustment limits of the attenuator, the signal is repositioned (along the X-axis) in step 127 and reloaded.

Figure 13:
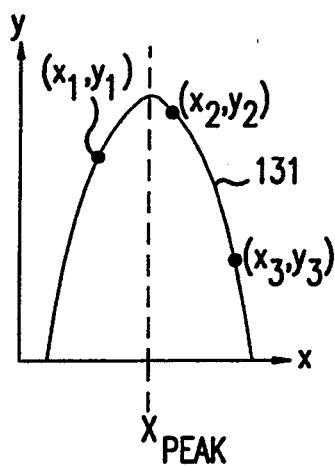
FIG. 13 is a graph illustrating the relative positions of coordinates $(x_1,y_1)$, $(x_2,y_2)$, $(x_3,y_3)$ used in the interpolation of step 128 in FIG. 13.

Once the signal is in range, it is set up for performing the cross correlation. The cross correlation window width is established at $5 \cdot T_p$ periods, where $T_p = (2\pi/\omega_o) = 1.0$ μsec for the signature waveform of FIG. 10(C). The cross correlation window is positioned to start $2 \cdot T_p$ periods to the left of $t_{onset}$, that is, at $(t_{onset} - 2 \cdot T_p)$. The early starting point here is adopted in order to include the possibility that an earlier signal onset time went undetected. Then cross correlation of the signal with the standard template waveform is performed (step 124). The X-coordinate at which there is the highest peak determines (step 125) a candidate transit time of the signature waveform. If the second highest peak is not greater than 90% of the height of the highest peak, then (in step 126) the highest peak is finally selected; if the second highest peak is greater than 90% of the height of the highest peak, then the signal is repositioned and reprocessed. The data samples from the finally selected highest peak are used to interpolate the X-coordinate of the actual peak, using the formula shown in step 128. The relative locations of the pertinent three data samples indicated by coordinates $(x_1, y_1)$, $(x_2, y_2)$, and $(x_3, y_3)$ are shown in FIG. 13. After interpolation to determine the location $x_{peak}$ on the X-axis of the selected peak, the actual transit time of the signature waveform is determined by adding the amount of system offset on the X-axis given to the signal in processing (step 129). As discussed above, based on the geometry of transducers 11 and 12, the bone velocity of the signature waveform can then be determined.

To enhance the accuracy of the velocity determination, the system may be calibrated against one or more standards (for example plastic solids) of known dimensions and known ultrasound velocities. The use of two or more such standards permits determination of a calibration offset to the transit time determination in accordance with FIG. 12. This offset compensates for inherent latencies in the system and variations in the geometry of the transducers and similar factors.

What is claimed is:

1. A system for externally measuring in a vertebrate subject characteristic behavior of an acoustic wave in a bone disposed within a body part, the system comprising:
   (a) first and second transducers;
   (b) mounting means for mounting the transducers in spaced relationship with respect to the bone, the mounting means including contact means for contacting the body part and defining a stable and repeatable position on the body part said contacting means including a plurality of contact buttons projecting in a common direction for contacting the body part;
   (c) signal excitation means coupled to the first transducer for causing the first transducer to produce an acoustic waveform that is propagated into the subject and received by the second transducer along a path that includes the bone;
   (d) characteristic determination means coupled to the second transducer for determining a characteristic of the behavior of the waveform along the path; and
   (e) a spring arrangement for mechanically biasing the transducers to urge them against the body part with substantially constant force.

2. A system according to claim 1, wherein the contact means includes four contact buttons in positions defining a rectangle.

3. A system according to claim 1, further comprising:
   means for mounting the buttons so that they are axially displaceable; and
   engagement sensing means for determining when each button has been placed firmly in contact with the body part.

4. A system according to claim 3, further comprising:
   inhibition means for inhibiting operation of the system unless and until the engagement sensing means has determined that each button has been placed firmly in contact with the body part.

5. A system according to claim 1, further comprising:
   a temperature sensor, disposed in one of the contact buttons, for sensing the temperature of the body part.

6. A system for externally measuring in a vertebrate subject characteristic behavior of an accoustic wave in a bone disposed within a body part, the system comprising:
   (a) first and second transducers;
   (b) mounting means for mounting the transducers in spaced relationship with respect to the bone;
   (c) signal excitation means for causing the first transducer to produce an acoustic waveform that is propagated into the subject and received by the second transducer along a path that includes the bone;
   (d) characteristic determination means for determining a characteristic of the behavior of the waveform along the path;
   wherein the transducers, the mounting means, the signal excitation means, and the characteristic determination means are all contained in a single hand-holdable assembly permitting the measurement to be taken while holding the assembly in one hand of the user.

7. A system according to claim 6, further comprising manual input means for receiving input data via manual entry and a display disposed within the housing.

8. A system according to claim 7, further comprising a database containing at least one of (i) a history of velocity determinations for one or more vertebrate subjects and (ii) statistical averages for groups of subjects.

9. A system according to claim 6, wherein each of the transducers has a central acoustic axis, and thee transducers are disposed so that their central axes form a fixed angle substantially less that 180 degrees.

10. A system for externally measuring in a vertebrate subject characteristic behavior of an acoustic wave in a bone disposed within a body part, the system comprising:
    (a) first and second transducers;
    (b) mounting means for mounting the transducers in spaced relationship with respect to the bone;
    (c) signal excitation means for causing the first transducer to produce an acoustic waveform that is propagated into the subject and received by the second transducer along a path that includes the bone;
    (d) characteristic determination means for determining a characteristic of the behavior of the waveform along the path;
    (e) a first housing for the transducers and the mounting means;
    (f) a second housing for the signal excitation means and the characteristic determination means;
    wherein the first housing is flexibly joined to the second housing to form a single hand-holdable assembly.

11. A system according to claim 10, further comprising a keypad and a display disposed within the second housing.

* * * * *

UNITED STATES PATENT AND TRADEMARK OFFICE
CERTIFICATE OF CORRECTION

PATENT NO. : 5,396,891
DATED : March 14, 1995
INVENTOR(S) : Hartwell H. Whitney

It is certified that error appears in the above-indentified patent and that said Letters Patent is hereby corrected as shown below:

On the title page item [75],

"Roy E. Laudenslager" should be deleted as inventor

Signed and Sealed this

Nineteenth Day of September, 1995

Attest:

BRUCE LEHMAN

*Attesting Officer*  *Commissioner of Patents and Trademarks*